(12) United States Patent  (10) Patent No.: US 8,128,688 B2
Ding et al.  (45) Date of Patent: Mar. 6, 2012

(54) CARBON COATING ON AN IMPLANTABLE DEVICE

(75) Inventors: Ni Ding, San Jose, CA (US); Gene Michal, San Francisco, CA (US); Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 239 days.

(21) Appl. No.: 11/820,560

(22) Filed: Jun. 19, 2007

(65) Prior Publication Data

US 2007/0298354 A1 Dec. 27, 2007

Related U.S. Application Data

(60) Provisional application No. 60/817,229, filed on Jun. 27, 2006.

(51) Int. Cl.
A61F 2/01 (2006.01)
(52) U.S. Cl. ........................ 623/1.42; 623/1.46
(58) Field of Classification Search ................ 623/1.11, 623/1.15, 1.46, 1.42
See application file for complete search history.

(56) References Cited

U.S. PATENT DOCUMENTS

| | | |
|---|---|---|
| 3,476,463 A | 11/1969 | Kreuzer |
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |

(Continued)

FOREIGN PATENT DOCUMENTS

CN 1241442 1/2000

(Continued)

OTHER PUBLICATIONS

International Search Report for PCT/US2007/014981, mailed Jun. 18, 2008, 17 pgs.

(Continued)

*Primary Examiner* — David Isabella
*Assistant Examiner* — Seema Swaminathan
(74) *Attorney, Agent, or Firm* — Squire Sanders (US) LLP

(57) ABSTRACT

A carbon coating on a stent having a bioactive agent covalently attached thereto and methods of making the same are described. The covalent attachment may be achieved via a photo-reactive chemical or a thermo-reactive chemical. In some embodiments, the carbon coating includes a diamond-like material. The bioactive agent may be heparin or superoxide dismutase enzyme or a mimetic thereof.

20 Claims, 1 Drawing Sheet

U.S. PATENT DOCUMENTS

| | | | |
|---|---|---|---|
| 4,776,337 | A | 10/1988 | Palmaz |
| 4,800,882 | A | 1/1989 | Gianturco |
| 4,816,339 | A | 3/1989 | Tu et al. |
| 4,818,559 | A | 4/1989 | Hama et al. |
| 4,850,999 | A | 7/1989 | Planck |
| 4,877,030 | A | 10/1989 | Beck et al. |
| 4,878,906 | A | 11/1989 | Lindemann et al. |
| 4,879,135 | A | 11/1989 | Greco et al. |
| 4,886,062 | A | 12/1989 | Wiktor |
| 4,886,870 | A | 12/1989 | D'Amore et al. |
| 4,902,289 | A | 2/1990 | Yannas |
| 4,977,901 | A | 12/1990 | Ofstead |
| 4,994,298 | A | 2/1991 | Yasuda |
| 5,019,090 | A | 5/1991 | Pinchuk |
| 5,028,597 | A | 7/1991 | Kodama et al. |
| 5,059,211 | A | 10/1991 | Stack et al. |
| 5,061,281 | A | 10/1991 | Mares et al. |
| 5,062,829 | A | 11/1991 | Pryor et al. |
| 5,084,065 | A | 1/1992 | Weldon et al. |
| 5,085,629 | A | 2/1992 | Goldberg et al. |
| 5,100,429 | A | 3/1992 | Sinofsky et al. |
| 5,104,410 | A | 4/1992 | Chowdhary |
| 5,108,417 | A | 4/1992 | Sawyer |
| 5,108,755 | A | 4/1992 | Daniels et al. |
| 5,112,457 | A | 5/1992 | Marchant |
| 5,123,917 | A | 6/1992 | Lee |
| 5,156,623 | A | 10/1992 | Hakamatsuka et al. |
| 5,163,951 | A | 11/1992 | Pinchuk et al. |
| 5,163,952 | A | 11/1992 | Froix |
| 5,163,958 | A | 11/1992 | Pinchuk |
| 5,167,614 | A | 12/1992 | Tessmann et al. |
| 5,192,311 | A | 3/1993 | King et al. |
| 5,197,977 | A | 3/1993 | Hoffman, Jr. et al. |
| 5,234,456 | A | 8/1993 | Silvestrini |
| 5,234,457 | A | 8/1993 | Andersen |
| 5,236,447 | A | 8/1993 | Kubo et al. |
| 5,279,594 | A | 1/1994 | Jackson |
| 5,282,860 | A | 2/1994 | Matsuno et al. |
| 5,289,831 | A | 3/1994 | Bosley |
| 5,290,271 | A | 3/1994 | Jernberg |
| 5,306,286 | A | 4/1994 | Stack et al. |
| 5,306,294 | A | 4/1994 | Winston et al. |
| 5,328,471 | A | 7/1994 | Slepian |
| 5,330,500 | A | 7/1994 | Song |
| 5,342,348 | A | 8/1994 | Kaplan |
| 5,342,395 | A | 8/1994 | Jarrett et al. |
| 5,342,621 | A | 8/1994 | Eury |
| 5,356,433 | A | 10/1994 | Rowland et al. |
| 5,380,976 | A | 1/1995 | Couch |
| 5,383,925 | A | 1/1995 | Schmitt |
| 5,385,580 | A | 1/1995 | Schmitt |
| 5,389,106 | A | 2/1995 | Tower |
| 5,399,666 | A | 3/1995 | Ford |
| 5,423,885 | A | 6/1995 | Williams |
| 5,441,515 | A | 8/1995 | Khosravi et al. |
| 5,443,458 | A | 8/1995 | Eury et al. |
| 5,443,500 | A | 8/1995 | Sigwart |
| 5,455,040 | A | 10/1995 | Marchant |
| 5,464,650 | A | 11/1995 | Berg et al. |
| 5,486,546 | A | 1/1996 | Mathiesen et al. |
| 5,500,013 | A | 3/1996 | Buscemi et al. |
| 5,502,158 | A | 3/1996 | Sinclair et al. |
| 5,507,799 | A | 4/1996 | Sumiya |
| 5,514,379 | A | 5/1996 | Weissleder et al. |
| 5,525,646 | A | 6/1996 | Lundgren et al. |
| 5,527,337 | A | 6/1996 | Stack et al. |
| 5,545,408 | A | 8/1996 | Trigg et al. |
| 5,554,120 | A | 9/1996 | Chen et al. |
| 5,556,413 | A | 9/1996 | Lam |
| 5,565,215 | A | 10/1996 | Gref et al. |
| 5,578,046 | A | 11/1996 | Liu et al. |
| 5,578,073 | A | 11/1996 | Haimovich et al. |
| 5,591,199 | A | 1/1997 | Porter et al. |
| 5,591,607 | A | 1/1997 | Gryaznov et al. |
| 5,593,403 | A | 1/1997 | Buscemi |
| 5,593,434 | A | 1/1997 | Williams |
| 5,599,301 | A | 2/1997 | Jacobs et al. |
| 5,599,922 | A | 2/1997 | Gryaznov et al. |
| 5,603,722 | A | 2/1997 | Phan et al. |
| 5,605,696 | A | 2/1997 | Eury et al. |
| 5,607,442 | A | 3/1997 | Fischell et al. |
| 5,607,467 | A | 3/1997 | Froix |
| 5,618,299 | A | 4/1997 | Khosravi et al. |
| 5,629,077 | A | 5/1997 | Turnlund et al. |
| 5,631,135 | A | 5/1997 | Gryaznov et al. |
| 5,632,771 | A | 5/1997 | Boatman et al. |
| 5,632,840 | A | 5/1997 | Campbell |
| 5,637,113 | A | 6/1997 | Tartaglia et al. |
| 5,649,977 | A | 7/1997 | Campbell |
| 5,656,186 | A | 8/1997 | Mourou et al. |
| 5,667,767 | A | 9/1997 | Greff et al. |
| 5,667,796 | A | 9/1997 | Otten |
| 5,670,161 | A | 9/1997 | Healy et al. |
| 5,670,558 | A | 9/1997 | Onishi et al. |
| 5,686,540 | A | 11/1997 | Kakizawa |
| 5,693,085 | A | 12/1997 | Buirge et al. |
| 5,700,286 | A | 12/1997 | Tartaglia et al. |
| 5,700,901 | A | 12/1997 | Hurst et al. |
| 5,707,385 | A | 1/1998 | Williams |
| 5,711,763 | A | 1/1998 | Nonami et al. |
| 5,716,981 | A | 2/1998 | Hunter et al. |
| 5,725,549 | A | 3/1998 | Lam |
| 5,726,297 | A | 3/1998 | Gryaznov et al. |
| 5,728,751 | A | 3/1998 | Patnaik |
| 5,733,326 | A | 3/1998 | Tomonto et al. |
| 5,733,330 | A | 3/1998 | Cox |
| 5,733,564 | A | 3/1998 | Lehtinen |
| 5,733,925 | A | 3/1998 | Kunz et al. |
| 5,735,896 | A * | 4/1998 | Amon et al. .................. 424/423 |
| 5,741,881 | A | 4/1998 | Patnaik |
| 5,756,457 | A | 5/1998 | Wang et al. |
| 5,756,476 | A | 5/1998 | Epstein et al. |
| 5,765,682 | A | 6/1998 | Bley et al. |
| 5,766,204 | A | 6/1998 | Porter et al. |
| 5,766,239 | A | 6/1998 | Cox |
| 5,766,710 | A | 6/1998 | Turnlund et al. |
| 5,769,883 | A | 6/1998 | Buscemi et al. |
| 5,770,609 | A | 6/1998 | Grainger et al. |
| 5,780,807 | A | 7/1998 | Saunders |
| 5,800,516 | A | 9/1998 | Fine et al. |
| 5,811,447 | A | 9/1998 | Kunz et al. |
| 5,824,049 | A | 10/1998 | Ragheb et al. |
| 5,830,178 | A | 11/1998 | Jones et al. |
| 5,830,461 | A | 11/1998 | Billiar |
| 5,830,879 | A | 11/1998 | Isner |
| 5,833,651 | A | 11/1998 | Donovan et al. |
| 5,834,582 | A | 11/1998 | Sinclair et al. |
| 5,836,962 | A | 11/1998 | Gianotti |
| 5,837,313 | A | 11/1998 | Ding et al. |
| 5,837,835 | A | 11/1998 | Gryaznov et al. |
| 5,840,083 | A | 11/1998 | Braach-Maksvytis |
| 5,851,508 | A | 12/1998 | Greff et al. |
| 5,853,408 | A | 12/1998 | Muni |
| 5,854,207 | A | 12/1998 | Lee et al. |
| 5,855,612 | A | 1/1999 | Ohthuki et al. |
| 5,855,618 | A | 1/1999 | Patnaik et al. |
| 5,858,746 | A | 1/1999 | Hubbell et al. |
| 5,865,814 | A | 2/1999 | Tuch |
| 5,868,781 | A | 2/1999 | Killion |
| 5,869,127 | A | 2/1999 | Zhong |
| 5,873,904 | A | 2/1999 | Ragheb et al. |
| 5,874,101 | A | 2/1999 | Zhong et al. |
| 5,874,109 | A | 2/1999 | Ducheyne et al. |
| 5,874,165 | A | 2/1999 | Drumheller |
| 5,876,743 | A | 3/1999 | Ibsen et al. |
| 5,877,263 | A | 3/1999 | Patnaik et al. |
| 5,879,713 | A | 3/1999 | Roth et al. |
| 5,888,533 | A | 3/1999 | Dunn |
| 5,891,192 | A | 4/1999 | Murayama et al. |
| 5,897,955 | A | 4/1999 | Drumheller |
| 5,906,759 | A | 5/1999 | Richter |
| 5,914,182 | A | 6/1999 | Drumheller |
| 5,916,870 | A | 6/1999 | Lee et al. |
| 5,922,005 | A | 7/1999 | Richter et al. |
| 5,942,209 | A | 8/1999 | Leavitt et al. |
| 5,948,428 | A | 9/1999 | Lee et al. |
| 5,954,744 | A | 9/1999 | Phan et al. |

| | | | |
|---|---|---|---|
| 5,957,975 A | 9/1999 | Lafont et al. | |
| 5,965,720 A | 10/1999 | Gryaznov et al. | |
| 5,971,954 A | 10/1999 | Conway et al. | |
| 5,976,182 A | 11/1999 | Cox | |
| 5,980,564 A | 11/1999 | Stinson | |
| 5,980,928 A | 11/1999 | Terry | |
| 5,980,972 A | 11/1999 | Ding | |
| 5,981,568 A | 11/1999 | Kunz et al. | |
| 5,986,169 A | 11/1999 | Gjunter | |
| 5,997,468 A | 12/1999 | Wolff et al. | |
| 6,010,445 A | 1/2000 | Armini et al. | |
| 6,015,541 A | 1/2000 | Greff et al. | |
| 6,042,606 A | 3/2000 | Frantzen | |
| 6,042,875 A | 3/2000 | Ding et al. | |
| 6,048,964 A | 4/2000 | Lee et al. | |
| 6,051,648 A | 4/2000 | Rhee et al. | |
| 6,056,993 A | 5/2000 | Leidner et al. | |
| 6,060,451 A | 5/2000 | DiMaio et al. | |
| 6,066,156 A | 5/2000 | Yan | |
| 6,071,266 A | 6/2000 | Kelley | |
| 6,074,659 A | 6/2000 | Kunz et al. | |
| 6,080,177 A | 6/2000 | Igaki et al. | |
| 6,080,488 A | 6/2000 | Hostettler et al. | |
| 6,083,258 A | 7/2000 | Yadav | |
| 6,093,463 A | 7/2000 | Thakrar | |
| 6,096,070 A | 8/2000 | Ragheb et al. | |
| 6,096,525 A | 8/2000 | Patnaik | |
| 6,099,562 A | 8/2000 | Ding et al. | |
| 6,099,563 A | 8/2000 | Zhong | |
| 6,103,230 A | 8/2000 | Billiar et al. | |
| 6,107,416 A | 8/2000 | Patnaik et al. | |
| 6,110,188 A | 8/2000 | Narciso, Jr. | |
| 6,110,483 A | 8/2000 | Whitbourne | |
| 6,113,629 A | 9/2000 | Ken | |
| 6,117,979 A | 9/2000 | Hendriks et al. | |
| 6,120,536 A | 9/2000 | Ding et al. | |
| 6,120,904 A | 9/2000 | Hostettler et al. | |
| 6,121,027 A | 9/2000 | Clapper et al. | |
| 6,125,523 A | 10/2000 | Brown et al. | |
| 6,127,173 A | 10/2000 | Eckstein et al. | |
| 6,129,761 A | 10/2000 | Hubbell | |
| 6,129,928 A | 10/2000 | Sarangapani et al. | |
| 6,131,266 A | 10/2000 | Saunders | |
| 6,150,630 A | 11/2000 | Perry et al. | |
| 6,153,252 A | 11/2000 | Hossainy et al. | |
| 4,776,337 A | 12/2000 | Palmaz | |
| 6,156,062 A | 12/2000 | McGuinness | |
| 6,159,951 A | 12/2000 | Karpeisky et al. | |
| 6,160,084 A | 12/2000 | Langer et al. | |
| 6,160,240 A | 12/2000 | Momma et al. | |
| 6,165,212 A | 12/2000 | Dereume et al. | |
| 6,166,130 A | 12/2000 | Rhee et al. | |
| 6,169,170 B1 | 1/2001 | Gryaznov et al. | |
| 6,171,609 B1 | 1/2001 | Kunz | |
| 6,174,330 B1 | 1/2001 | Stinson | |
| 6,177,523 B1 | 1/2001 | Reich et al. | |
| 6,179,817 B1 | 1/2001 | Zhong | |
| 6,183,505 B1 | 2/2001 | Mohn, Jr. et al. | |
| 6,187,045 B1 | 2/2001 | Fehring et al. | |
| 6,197,051 B1 | 3/2001 | Zhong | |
| 6,210,715 B1 | 4/2001 | Starling et al. | |
| 6,224,626 B1 | 5/2001 | Steinke | |
| 6,228,845 B1 | 5/2001 | Donovan et al. | |
| 6,231,590 B1 | 5/2001 | Slaikeu et al. | |
| 6,240,616 B1 | 6/2001 | Yan | |
| 6,245,076 B1 | 6/2001 | Yan | |
| 6,245,103 B1 | 6/2001 | Stinson | |
| 6,248,344 B1 | 6/2001 | Ylanen et al. | |
| 6,251,135 B1 | 6/2001 | Stinson et al. | |
| 6,251,142 B1 | 6/2001 | Bernacca et al. | |
| 6,254,634 B1 | 7/2001 | Anderson et al. | |
| 6,260,976 B1 | 7/2001 | Endou et al. | |
| 6,273,913 B1 | 8/2001 | Wright et al. | |
| 6,281,262 B1 | 8/2001 | Shikinami | |
| 6,284,333 B1 | 9/2001 | Wang et al. | |
| 6,287,332 B1 | 9/2001 | Bolz et al. | |
| 6,290,721 B1 | 9/2001 | Heath | |
| 6,293,966 B1 | 9/2001 | Frantzen | |
| 6,295,168 B1 | 9/2001 | Hoffnagle et al. | |
| 6,303,901 B1 | 10/2001 | Perry et al. | |
| 6,312,459 B1 | 11/2001 | Huang et al. | |
| 6,327,772 B1 | 12/2001 | Zadno-Azizi et al. | |
| 4,733,665 C2 | 1/2002 | Palmaz | |
| 6,375,826 B1 | 4/2002 | Wang et al. | |
| 6,379,381 B1 | 4/2002 | Hossainy et al. | |
| 6,387,121 B1 | 5/2002 | Alt | |
| 6,388,043 B1 | 5/2002 | Langer et al. | |
| 6,395,326 B1 | 5/2002 | Castro et al. | |
| 6,409,761 B1 | 6/2002 | Jang | |
| 6,423,092 B2 | 7/2002 | Datta et al. | |
| 6,461,632 B1 | 10/2002 | Gogolewski | |
| 6,464,720 B2 | 10/2002 | Boatman et al. | |
| 6,475,779 B2 | 11/2002 | Mathiowithz et al. | |
| 6,479,565 B1 | 11/2002 | Stanley | |
| 6,485,512 B1 | 11/2002 | Cheng | |
| 6,492,615 B1 | 12/2002 | Flanagan | |
| 6,494,908 B1 | 12/2002 | Huxel et al. | |
| 6,495,156 B2 | 12/2002 | Wenz et al. | |
| 6,511,748 B1 | 1/2003 | Barrows | |
| 6,514,734 B1 * | 2/2003 | Clapper et al. | 435/180 |
| 6,517,888 B1 | 2/2003 | Weber | |
| 6,521,865 B1 | 2/2003 | Jones et al. | |
| 6,527,801 B1 | 3/2003 | Dutta | |
| 6,537,589 B1 | 3/2003 | Chae et al. | |
| 6,539,607 B1 | 4/2003 | Fehring et al. | |
| 6,540,777 B2 | 4/2003 | Stenzel | |
| 6,554,854 B1 | 4/2003 | Flanagan | |
| 6,563,080 B2 | 5/2003 | Shapovalov et al. | |
| 6,563,998 B1 | 5/2003 | Farah | |
| 6,565,599 B1 | 5/2003 | Hong et al. | |
| 6,569,191 B1 | 5/2003 | Hogan | |
| 6,569,193 B1 | 5/2003 | Cox et al. | |
| 6,572,672 B2 | 6/2003 | Yadav et al. | |
| 6,574,851 B1 | 6/2003 | Mirizzi | |
| 6,582,472 B2 | 6/2003 | Hart | |
| 6,585,755 B2 | 7/2003 | Jackson et al. | |
| 6,592,614 B2 | 7/2003 | Lenker et al. | |
| 6,592,617 B2 | 7/2003 | Thompson | |
| 6,613,072 B2 | 9/2003 | Lau et al. | |
| 6,620,194 B2 | 9/2003 | Ding et al. | |
| 6,626,939 B1 | 9/2003 | Burnside | |
| 6,635,269 B1 | 10/2003 | Jennissen | |
| 6,645,243 B2 | 11/2003 | Vallana et al. | |
| 6,656,162 B2 | 12/2003 | Santini, Jr. et al. | |
| 6,664,335 B2 | 12/2003 | Krishnan | |
| 6,666,214 B2 | 12/2003 | Canham | |
| 6,667,049 B2 | 12/2003 | Janas et al. | |
| 6,669,723 B2 | 12/2003 | Killion et al. | |
| 6,676,697 B1 | 1/2004 | Richter | |
| 6,679,980 B1 | 1/2004 | Andreacchi | |
| 6,689,375 B1 | 2/2004 | Wahlig et al. | |
| 6,695,920 B1 | 2/2004 | Pacetti et al. | |
| 6,696,667 B1 | 2/2004 | Flanagan | |
| 6,706,273 B1 | 3/2004 | Roessler | |
| 6,709,379 B1 | 3/2004 | Brandau et al. | |
| 6,719,934 B2 | 4/2004 | Stinson | |
| 6,719,989 B1 | 4/2004 | Matsushima et al. | |
| 6,720,402 B2 | 4/2004 | Langer et al. | |
| 6,746,773 B2 | 6/2004 | Llanos et al. | |
| 6,752,826 B2 | 6/2004 | Holloway et al. | |
| 6,753,007 B2 | 6/2004 | Haggard et al. | |
| 6,764,505 B1 | 7/2004 | Hossainy et al. | |
| 6,780,261 B2 | 8/2004 | Trozera | |
| 6,800,783 B2 | 10/2004 | Springer et al. | |
| 6,801,368 B2 | 10/2004 | Coufal et al. | |
| 6,805,898 B1 | 10/2004 | Wu et al. | |
| 6,818,063 B1 | 11/2004 | Kerrigan | |
| 6,822,186 B2 | 11/2004 | Strassl et al. | |
| 6,846,323 B2 | 1/2005 | Yip et al. | |
| 6,852,946 B2 | 2/2005 | Groen et al. | |
| 6,858,680 B2 | 2/2005 | Gunatillake et al. | |
| 6,867,389 B2 | 3/2005 | Shapovalov et al. | |
| 6,878,758 B2 | 4/2005 | Martin et al. | |
| 6,891,126 B2 | 5/2005 | Matile | |
| 6,899,729 B1 | 5/2005 | Cox et al. | |
| 6,911,041 B2 | 6/2005 | Zscheeg | |
| 6,913,762 B2 | 7/2005 | Caplice et al. | |
| 6,926,733 B2 | 8/2005 | Stinson | |

| | | | |
|---|---|---|---|
| 6,943,964 B1 | 9/2005 | Zhang et al. | |
| 6,981,982 B2 | 1/2006 | Armstrong et al. | |
| 6,981,987 B2 | 1/2006 | Huxel et al. | |
| 7,022,132 B2 | 4/2006 | Kocur | |
| 7,128,737 B1 | 10/2006 | Goder et al. | |
| 7,163,555 B2 | 1/2007 | Dinh | |
| 7,166,099 B2 | 1/2007 | Devens, Jr. | |
| 7,226,475 B2 | 6/2007 | Lenz et al. | |
| 2001/0044652 A1 | 11/2001 | Moore | |
| 2002/0004060 A1 | 1/2002 | Heublein et al. | |
| 2002/0065553 A1 | 5/2002 | Weber | |
| 2002/0111590 A1 | 8/2002 | Davila et al. | |
| 2002/0190038 A1 | 12/2002 | Lawson | |
| 2003/0033001 A1 | 2/2003 | Igaki | |
| 2003/0039689 A1 | 2/2003 | Chen et al. | |
| 2003/0065355 A1 | 4/2003 | Weber | |
| 2003/0069632 A1* | 4/2003 | De Scheerder et al. | 623/1.15 |
| 2003/0093107 A1 | 5/2003 | Parsonage et al. | |
| 2003/0105518 A1 | 6/2003 | Dutta | |
| 2003/0105530 A1 | 6/2003 | Pirhonen | |
| 2003/0108588 A1 | 6/2003 | Chen | |
| 2003/0153971 A1 | 8/2003 | Chandrasekaran | |
| 2003/0155328 A1 | 8/2003 | Huth | |
| 2003/0171053 A1 | 9/2003 | Sanders | |
| 2003/0187495 A1 | 10/2003 | Cully et al. | |
| 2003/0187496 A1 | 10/2003 | Kirk et al. | |
| 2003/0208259 A1 | 11/2003 | Penhasi | |
| 2003/0209835 A1 | 11/2003 | Chun et al. | |
| 2003/0226833 A1 | 12/2003 | Shapovalov et al. | |
| 2003/0236563 A1 | 12/2003 | Fifer | |
| 2004/0093077 A1 | 5/2004 | White et al. | |
| 2004/0098090 A1 | 5/2004 | Williams et al. | |
| 2004/0098095 A1 | 5/2004 | Burnside et al. | |
| 2004/0106987 A1 | 6/2004 | Palasis et al. | |
| 2004/0111149 A1 | 6/2004 | Stinson | |
| 2004/0126405 A1 | 7/2004 | Sahatjian | |
| 2004/0127970 A1 | 7/2004 | Saunders | |
| 2004/0143180 A1 | 7/2004 | Zhong et al. | |
| 2004/0143317 A1 | 7/2004 | Stinson et al. | |
| 2004/0167610 A1 | 8/2004 | Fleming, III | |
| 2005/0004663 A1 | 1/2005 | Llanos et al. | |
| 2005/0021131 A1 | 1/2005 | Venkatraman et al. | |
| 2005/0087520 A1 | 4/2005 | Wang et al. | |
| 2005/0111500 A1 | 5/2005 | Harter et al. | |
| 2005/0147647 A1 | 7/2005 | Glauser et al. | |
| 2005/0157382 A1 | 7/2005 | Kafka et al. | |
| 2005/0211680 A1 | 9/2005 | Li et al. | |
| 2006/0033240 A1 | 2/2006 | Weber et al. | |
| 2006/0120418 A1 | 6/2006 | Harter et al. | |
| 2006/0147413 A1* | 7/2006 | Alferiev et al. | 424/78.27 |
| 2007/0198080 A1* | 8/2007 | Ding et al. | 623/1.38 |
| 2008/0286588 A1* | 11/2008 | Burgess et al. | 428/469 |
| 2011/0060403 A9* | 3/2011 | Nakatani et al. | 623/1.49 |

FOREIGN PATENT DOCUMENTS

| | | |
|---|---|---|
| DE | 44 07 079 | 9/1994 |
| DE | 197 31 021 | 1/1999 |
| DE | 198 56 983 | 12/1999 |
| DE | 29724852 | 2/2005 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 556 940 | 8/1993 |
| EP | 0 578 998 | 1/1994 |
| EP | 0583170 | 2/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0714641 | 6/1996 |
| EP | 0 842729 | 5/1998 |
| EP | 0842729 | 5/1998 |
| EP | 0 970 711 | 1/2000 |
| EP | 1210 922 | 6/2002 |
| EP | 1 754 684 | 2/2007 |
| FR | 2 654 345 | 5/1991 |
| GB | 2 247 696 | 3/1992 |
| JP | 4-33791 | 2/1992 |
| JP | 7-124766 | 5/1995 |
| JP | 10-166156 | 6/1998 |
| JP | 2003-53577 | 2/2003 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/27587 | 10/1995 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/20429 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 02/38325 | 5/2002 |
| WO | WO 03/015978 | 2/2003 |
| WO | WO 03/057075 | 7/2003 |
| WO | WO 03/086496 | 10/2003 |
| WO | WO 2004/019820 | 3/2004 |
| WO | WO 2004/023985 | 3/2004 |
| WO | WO 2004/062533 | 7/2004 |
| WO | WO 2004/112863 | 12/2004 |
| WO | WO 2005/023480 | 3/2005 |
| WO | WO 2006/060836 | 6/2006 |

OTHER PUBLICATIONS

U.S. Appl. No. 10/317,435, filed Dec. 11, 2002, Hossainy et al.
Acquarulo et al., *Enhancing Medical Device Performance with Nanocomposite Poly*, Med. Device Link, www.devicelink.com/grabber.php3?URL downloaded Mar. 26, 2007, 4 pgs.
Anonymous, *Bioabsorbable stent mounted on a catheter having optical coherence tomography capabilities*, Research Disclosure, Sep. 2004, pp. 1159-1162.
Ansari, *End-to-end tubal anastomosis using an absorbable stent*, Fertility and Sterility, vol. 32(2), pp. 197-201 (Aug. 1979).
Ansari, *Tubal Reanastomosis Using Absorbable Stent*, International Journal of Fertility, vol. 23(4), pp. 242-243 (1978).
Casper et al., *Fiber-Reinforced Absorbable Composite for Orthopedic Surgery*, Polymeric Materials Science and Engineering, vol. 53 pp. 497-501 (1985).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).
Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Eidelman et al., *Characterization of Combinatorial Polymer Blend Composition Gradients by FTIR Microspectroscopy*, J. Res. Natl. Inst. Standards and Technol., vol. 109, No. 2, pp. 219-231 (2004).
Fan et al., *Plasma Absorption of Femtosecond Laser Pulses in Dielectrics*, J. of Heat Transfer, vol. 124, pp. 275-283 (2002).
He et al., *Assessment of Tissue Blood Flow Following Small Artery Welding with an Intraluminal Dissolvable Stent*, Microsurgery, vol. 19(3), pp. 148-152 (1999).

Hoffnagle et al., *Design and performance of a refractive optical system that converts a Gaussian to a flattop beam*, Applied Optics, vol. 39, No. 30 pp. 5488-5499 (2000).

Kubies et al., *Microdomain Structure In polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

NanoComposix, products, www.nanocomposix.com, downloaded Mar. 26, 2007, 2 pgs.

Nanosiliver, Photocatalyst and Nanocomposite Material, http://eng.nanocomposite.net downloaded Mar. 26, 2007, 1 pg.

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Sun et al., "Inert gas beam delivery for ultrafast laser micromachining at ambient pressure", Am. Inst. Of Physics, 6 pgs.

Tamai et al., *Initial and 6-Month Results of Biodegradable Poly-I-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

von Recum et al., *Degradation of polydispersed poly(L-lactic acid) to modulate lactic acid release*, Biomaterials, vol. 16, pp. 441-445 (1995).

Zhang et al., "Single-element laser beam shaper for uniform flat-top profiles" Optics Express, vol. 11, No. 16, pp. 1942-1948 (2003).

Venkatraman, C., et al., "Tribological Properties of Diamond-Like Nanocomposite Coatings at High Tempeartures," Surface and Coatings Technology, 115: 215-221 (1999).

* cited by examiner

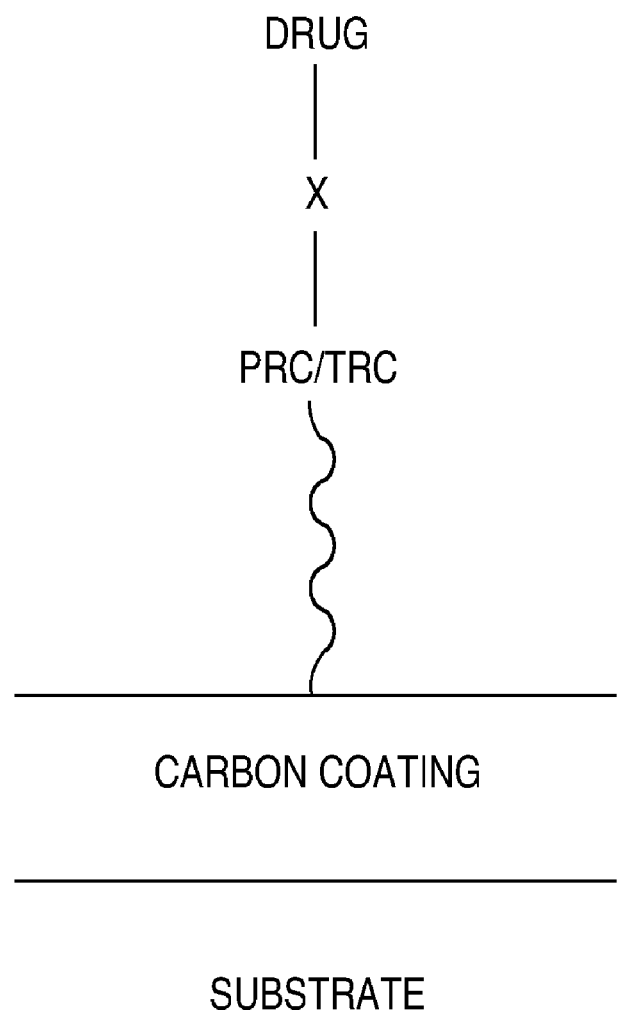

CARBON COATING ON AN IMPLANTABLE DEVICE

CROSS-REFERENCE TO RELATED APPLICATION

This is a non-provisional application which claims the benefit of U.S. provisional application No. 60/817,229, filed Jun. 27, 2006, the teaching of which is incorporated herein by reference in its entirety.

FIELD OF THE INVENTION

This invention generally relates to covalent attachment of biologically active agents to a carbon coated stent.

DESCRIPTION OF THE BACKGROUND

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

Although stents work well mechanically, the chronic issues of restenosis and, to a lesser extent, stent thrombosis remain. Pharmacological therapy in the form of a drug delivery stent appears to be a feasible means to tackle these issues. Polymeric coatings placed onto the stent serve to act both as the drug reservoir and to control the release of the drug. One of the commercially available polymer coated products is stents manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

Subacute thrombosis and neointimal hyperplasia are considered to be the leading complications after stenting. Various factors are believed to be involved in the process. Methods for reducing thrombosis and restenosis have been previously proposed. However, those methods are less satisfactory for reducing late thrombosis and/or restenosis associated with stenting.

Therefore, there is a need for a coating on a stent that provides for reduction of early and late thrombosis and/or restenosis.

The embodiments disclosed herein address the above described problems.

SUMMARY OF THE INVENTION

The present invention describes a method for forming a carbon coating on an implantable device. The carbon coating includes a bioactive agent attached thereto. Combination of a bioactive agent (e.g., SODm, pegylated active agent and/or heparin) and carbon can address more than one factor leading to neointimal hyperplasia or subacute thrombosis and may thus reduce early or late thrombosis, and restenosis. Therefore, when the bioactive agent is removed by the body after implantation, the underlying carbon surface can still provide high degree of biocompatibility.

As used herein, the carbon coating generally includes two to four covalently linked carbon (C), hydrogen (H), silicon (Si), and oxygen (O) atoms.

In some embodiments, a bioactive agent can be attached to the carbon coating without surface modification of the carbon coating. For example, a carbon coating can be exposed to a photo-reactive chemical (PRC) or a thermo-reactive chemical (TRC), which includes at least one reactive group. A light or heat can then be applied to the carbon coating and the PRC or TRC. The PRC or TRC can then generate radicals which can extract hydrogen radicals from the carbon surface to allow the PRC or TRC to covalently link to the carbon coating surface. A bioactive agent can then be covalently attached to the PRC or TRC via the at least one reactive group.

In some embodiments, the attachment of the bioactive agent to the PRC or TRC can be carried out prior to attaching the PRC or TRC to the carbon coating so as to form a carbon coating having bioactive agents attached thereto via the PRC or TRC.

Any bioactive agent can be attached to a carbon coating according to the method described herein. An implantable device bearing such a carbon coating can be used to treat, prevent, or ameliorate a disorder in a human being by implanting in the human being (e.g., a patient) an implantable device described herein. The disorder can be, e.g., atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

BRIEF DESCRIPTION OF THE DRAWINGS

FIG. 1 illustrates a carbon coating according to an embodiment of the invention.

DETAILED DESCRIPTION

The present invention describes a method for forming a carbon coating on an implantable device. The carbon coating includes a bioactive agent attached thereto. Combination of a bioactive agent (e.g., SODm, pegylated active agent and/or heparin) and carbon can address more than one factor leading to neointimal hyperplasia or subacute thrombosis and may thus reduce early or late thrombosis, and restenosis. Therefore, when the bioactive agent is removed by the body after implantation, the underlying carbon surface can still provide high degree of biocompatibility.

As used herein, the carbon coating generally includes two to four covalently linked carbon (C), hydrogen (H), silicon (Si), and oxygen (O) atoms.

In some embodiments, a bioactive agent can be attached to the carbon coating without surface modification of the carbon coating. For example, a carbon coating can be exposed to a photo-reactive chemical (PRC) or a thermo-reactive chemical (TRC), which includes at least one reactive group. A light or heat can then be applied to the carbon coating and the PRC or TRC. The PRC or TRC can then generate radicals which can extract hydrogen radicals from the carbon surface to allow the PRC or TRC to covalently link to the carbon coating surface. A bioactive agent can then be covalently attached to the PRC or TRC via the at least one reactive group.

In some embodiments, the attachment of the bioactive agent to the PRC or TRC can be carried out prior to attaching the PRC or TRC to the carbon coating so as to form a carbon coating having bioactive agents attached thereto via the PRC or TRC.

Any bioactive agent can be attached to a carbon coating according to the method described herein. An implantable device bearing such a carbon coating can be used to treat, prevent, or ameliorate a disorder in a human being by implanting in the human being (e.g., a patient) an implantable device described herein. The disorder can be, e.g., atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

Carbon Coating

A carbon coating can be deposited via plasma assisted chemical vapor deposition (CVD) from ART, Inc. This coating has good adhesion and mechanical properties as a stent coating. An ART carbon coating can contain four covalently linked carbon (C), hydrogen (H), silicon (Si), and oxygen ($|O|_{[AT]}$) atoms. The coating comprises a diamond-like material having an interpenetrating network, one of which is rich in carbon while the other is rich in silicon. Another example is diamond-like carbon coating, which may contain only two elements, i.e. carbon and hydrogen.

In some embodiments, the carbon coating can include other elements or materials such as a metal element(s) such as iron (Fe), silver (Ag), gold (Au), Magnesium (Mg), calcium (Ca), potassium (K), or sodium (Na), titanium, zirconium, niobium, tantalum, and hafnium, metal compound (s) such as titanium nitride, titanium carbonitride, titanium carbide, and/or other non-metal elements such as nitrogen, phosphorus, or boron.

In some embodiments, the carbon coating can further include a ceramic material.

The carbon coating can be formed by established methods. For example, a chemical vapor deposition process can be used to form a diamond-like coating is known in the literature (Handbook of Chemical Vapor Deposition-Principles, Technology and Application, $2^{nd}$ edition by Hugh O. Pierson, Noyes Publication).

Bioactive Agents

As used herein, the term bioactive agent refers to an agent the presence of which elicits a desirable biological response in a tissue to which the agent is exposed in a mammal, e.g., a patient. The bioactive agent can be, e.g., a drug, polymer, protein, peptide or a drug. In some embodiments, the term "bioactive agent" is used interchangeably with "drug."

In some embodiments, the bioactive agents can be SODm, heparin, polyethylene glycol/oxide, sialic acid, hyaluronic acid, polyethylene glycol/oxide-attached bioactive agents, synthetic peptides and natural proteins, nitric oxide donor molecules or combinations of thereof.

The term "SOD" refers to endogeneous superoxide dismutase enzyme. SODm refers to mimetics of the SOD enzyme. The term "mimetic" is sometimes referred to as and used interchangeably with the term "mimics."

SOD can have important effects on vascular pathophysiology. For example, SOD1-deficient mice have been found to produce more superoxide than their wild-type controls and have decreased endothelium-dependent and -independent vasodilation. SOD1 overexpression in mice causes a decrease in vascular smooth muscle cell (VSMC) proliferation in response to endothelial growth factor (EGF) but no change in the aortic hypertrophic response to Angiotensin II. A separate study with mice overexpressing SOD1 on the apoE$^{-/-}$ background showed no significant effect on aortic atherosclerotic lesion area. Total SOD2 deficiency is lethal in mice, and although partial SOD2 deficiency has been shown to cause an increase in atherosclerotic lesion formation at arterial branch points, there was no effect on vasomotor responses to serotonin, PGF2α, or acetylcholine at baseline or after inhibition of SOD 1 and SOD3 with diethyldithiocarbamate. The second most abundant SOD isoform in blood vessels is SOD3, which is predominantly produced by VSMCs, but because its location in the interstitium between ECs and VSMCs it is thought to be essential for endothelial-dependent vasodilation by protecting NO as it diffuses from the ECs to the VSMCs. These differences in the regulation of vascular tone or in the formation of atherosclerotic lesions indicate the potential importance of the subcellular localization of antioxidant systems in the modulation of local oxidant signaling.

SODm includes any compounds that provides for functions similar to those of SOD. Such examples of SODm include peptide mimetics of SOD. Another example of SODm is a manganese-based, low molecular weight (MW=543) SOD complex with the structure illustrated below.

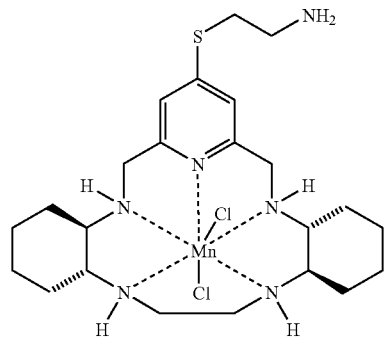

In some embodiments, the bioactive agent can be a polymer, or polymeric conjugate of a bioactive agent, that imparts a favorable biological property or properties to the carbon coating. Such polymers, or polymer conjugates, can be, e.g., polyethylene glycol (PEG) or polyethylene oxide (PEO), polyethylene glycol/oxide derivative, sodium hyaluronate and its derivatives, sialic acid, synthetic peptides or natural proteins, synthetic or natural polysaccharides, aloe derived pectin (DelSite Inc.), recombinant human gelatin (Fibrogen), etc.

As used herein, the term heparin includes sodium heparin, low molecular weight heparins, heparin derivative, heparinoids, or fragments of these.

The bioactive agents described above can also be pegylated active agents. Pegylated bioactive agents are active agents modified or otherwise derivatized with poly(ethylene glycol). The term pegylated bioactive agent are also referred as "pegylated drug" or "pegylated active agent".

In some embodiments, the bioactive agent or drug described herein can specifically exclude any one or more of the above listed agents or drug.

Attaching Bioactive Agents

In some embodiments, attachment of the bioactive agents to the carbon coating can be induced via photo activation. For example, photo-reactive chemical(s) (PRC) can extract hydrogen on the surface in the form of C—H or Si—H bonds, and covalently couple directly to the surface. If the PRC contains chemically reactive groups, bioactive agents, such as SODm and/or heparin, can be bound to the PRC. As a result, a desired biological agent can be covalently grafted to the carbon surface. An example is shown in FIG. 1 where X represents a reactive group on the PRC or TRC which covalently links the drug to the PRC or TRC.

In some embodiments, attachment of the bioactive agents to the carbon coating can be induced via thermal activation. For example, thermo-reactive chemical(s) (TRC) can extract hydrogen on the surface in the form of C—H or Si—H bonds, and covalently couple directly to the surface. If the TRC contains chemically reactive groups, bioactive agents, such as SODm and/or heparin, can be bound to the PRC. As a result, a desired biological agent can be covalently grafted to the carbon surface. Examples of PRCs include, but are not limited to, the ones from the benzophenone family, i.e. benzophenone tetracarboxylic dianhydride, benzoylbenzoic acid, benzoyl benzoyl chloride, 4-benzoylbenzoic acid N-hydroxysuccinimide ester, benzoyl benzoyl amine, or from azide family, i.e. substituted phenyl azide and substituted acyl azide.

TRC typically involves the compounds possessing O—O, S—S, N—O, N=N bonds. Examples of TRCs include, but are not limited to acyl peroxide (e.g. acetyl and benzoyl peroxides), alkyl peroxide (e.g. cumyl and t-butyl peroxide), hydroperoxide (e.g. t-butyl and cumyl hydroperoxide), perester (e.g. t-butyl perbenzoate), azo compound (e.g. Azobisisobutylonitrile (AIBN)), and disulfides.

The hydrogen extraction can be initiated by light, e.g. ultraviolet (UV), exposure of the PRC entity or thermal exposure of the TRC entity. The derivatives of PRC and TRC compounds contain the chemical reactive groups as a coupling agent. The coupling reaction between PRC or TRC to the biologically active agent will be dependent on the specific structure of the PRC or TRC molecule but can be readily carried out by an ordinary artisan. For example, an amine functional group on SODm can react with an anhydride or acyl chloride of substituted benzophenone. The PRC or TRC can be coupled to the carbon surface first and then coupled with the biological agent, or vice versa.

For example, some examples of reactive group on PRC or TRC include, but are not limited to, an acid group (e.g., carboxylic group, sulfonic acid group, phosphoric acid group, phosphonic acid group, sulfuric acid group), hydroxyl group, amino group, thiol group, aldehyde, keto, acetal, etc. The bioactive agents either include or can be made to include a reactive group such as an acid group (e.g., carboxylic group, sulfonic acid group, phosphoric acid group, phosphonic acid group, sulfuric acid group), hydroxyl group, amino group, thiol group, aldehyde, keto, acetal, etc.

Attachment of the bioactive agent to the carbon coating can then be readily achieved by reaction between the reactive group on the PRC or TRC and the reactive group on the bioactive agent. For example, the carboxylic acid group of the PRC or TRC molecule can form an ester bond with a drug molecule via an established procedure in the art of organic synthesis. Generally, the attachment the bioactive agent to the PRC or TRC via a carboxylic acid group can be achieved according to Scheme 1 as described below.

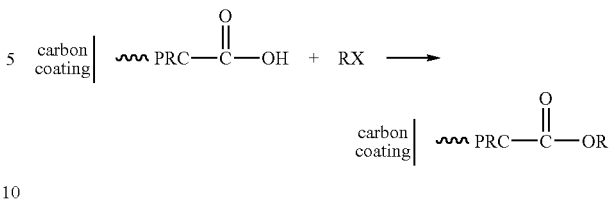

In Scheme 1, R represents a drug molecule or a derivative thereof. X represents a leaving group attached to the drug molecule. For example, X can be OH, a halo group, mesylate or tosyl group, and any other groups capable of leaving the drug molecule in forming the drug/PRC ester bond. PRC can also be TRC. Alternatively, the attachment can be achieved via a hydroxyl group in the PRC molecule and a carboxylic acid in R, as shown in Scheme 2.

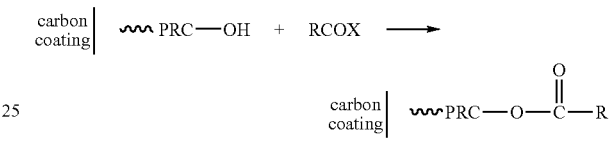

In Scheme 2, R represents a drug molecule or a derivative thereof. X represents a leaving group attached to the drug molecule. For example, X can be OH, a halo group, an imidazole group, an o-Acylurea group, an NHS or Sulfo NHS group, and any other groups capable of leaving the drug molecule in forming the drug/PRC ester bond. For example, mesylate or tosylate can be leaving groups since they can be used to derivatize —OH functional materials. PRC can also be TRC. In alternate embodiments, the PRC or TRC can be derivatized on the stent to have a good leaving group (e.g., imidazole via reaction with carbonyl di-imidazole), and this can subsequently react with a hydroxyl or amine group on the drug or bioactive polymer.

In some other embodiments, the attachment described herein can be achieved via forming an imine Schiff base by PRC-CHO or TRC-CHO with an amine-containing drug (Scheme 3) or vice versa. As shown in Scheme 3, the aldehyde group of PRC-CHO can react with the amine group of an amine-containing drug to form an imine Schiff base, which is hydrolytically unstable and can release the amine-containing drug under in vivo conditions. An alternative strategy for attaching a bioactive agent can be carried out by the reaction of the amino group of PRC-NH$_2$ or TRC-NH$_2$ with a keto group on the drug molecule to form an imine Schiff base linkage. In some embodiments, the stabilization of the Schiff base can be achieved by hydrogenation using for example, the reducing agent Sodium cyanoborohydride.

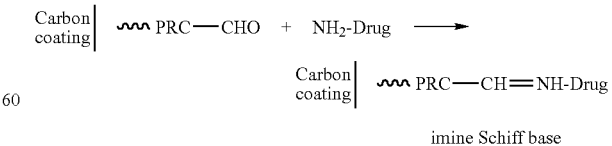

Again, in Scheme 3, PRC can be replaced with TRC.

In still some other embodiments, the attachment described herein can be achieved via forming an acetal or hemi-acetal by PRC-CHO or TRC-CHO with a hydroxyl group or hydroxyl groups on a drug (Scheme 4) or vice versa. The acetal or hemi-acetal can undergo hydrolysis under in vivo conditions to release the bioactive agent. As shown in Scheme 4, the aldehyde group of PRC-CHO on the carbon coating can react with hydroxyl group or groups on a drug to form a prodrug with an acetal linkage or hemi-acetal linkage. Alternatively, the hydroxyl group or groups can react with an aldehyde or keto group on a drug to form a prodrug with an acetal linkage or hemi-acetal linkage.

structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bris- Scheme 4

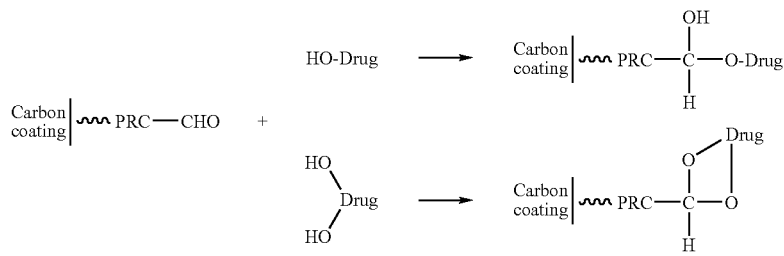

Other methods of attaching the bioactive agent to the carbon coating are well documented and readily appreciable by an ordinary artisan (see, for example, Larock, Comprehensive Organic Transformations: A Guide to Functional Group Preparations, John Wiley & Sons, Inc., Copyright 1999).

In some embodiments, the attachment of the bioactive agent to the PRC or TRC can be carried out prior to attaching the PRC or TRC to the carbon coating so as to form a carbon coating having bioactive agents attached thereto via the PRC or TRC. The chemistry for achieving this is the same as described above.

Other Bioactive Agents

The bioactive agent can include other agents that are not listed above. Such other bioactive agents can be any bioactive agent, which is a therapeutic, prophylactic, or diagnostic agent. These agents can have anti-proliferative or anti-inflammmatory properties or can have other properties such as antineoplastic, antiplatelet, anti-coagulant, anti-fibrin, antithrombonic, antimitotic, antibiotic, antiallergic, and antioxidant. The agents can be cystostatic agents, agents that promote the healing of the endothelium such as NO releasing or generating agents, agents that attract endothelial progenitor cells, or agents that promote the attachment, migration and proliferation of endothelial cells (e.g., natriuretic peptide such as CNP, ANP or BNP peptide or an RGD or cRGD peptide), while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and tol-Myers Squibb Co., Stamford, Conn.). Examples of such antiplatelets, anticoagulants, antifibrin, and antithrombins include hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, or combinations thereof. Examples of cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The bioactive agents described above can also be pegylated bioactive agents. Examples of such pegylated bioactive agents can be pegylated sirolimus, pegylated everolimus, pegylated zotarolimus, pegylated paclitaxel, pegylated proteins, pegylated peptides, etc.

In some embodiments, the bioactive agent or drug described herein can specifically exclude any one or more of the above listed agents or drug.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), heart valve prostheses, cerebrospinal fluid shunts, pacemaker electrodes, catheters, and endocardial leads (e.g., FINELINE and ENDOTAK, available from Abbott Vascular, Santa Clara, Calif.), anastomotic devices and connectors, orthopedic implants such as screws, spinal implants, electro-stimulatory devices. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, the bioactive agents can be released from a carbon coating described herein on a medical device (e.g., stent) during delivery and (in the case of a stent) expansion of the device, or thereafter, and released at a desired rate and for a predetermined duration of time at the site of implantation.

Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, femoral, popliteal, renal, carotid and coronary arteries.

For implantation of a stent, an angiogram is first performed to determine the appropriate positioning for stent therapy. An angiogram is typically accomplished by injecting a radiopaque contrast agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described features may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. An implantable device comprising a carbon coating and a bioactive agent attached thereto;
    wherein the bioactive agent is covalently attached to a photo-reactive chemical (PRC) which is in turn covalently attached directly to the carbon coating;
    wherein the carbon coating comprises covalently linked carbon (C), hydrogen (H), silicon (Si), and oxygen (O) atoms; and
    wherein the carbon coating comprises a diamond-like material.

2. The implantable device of claim 1, wherein the bioactive agent is attached to the PRC via at least one reactive group.

3. The implantable device of claim 1, wherein the PRC is a compound in the benzophenone family or a compound in the azide family.

4. The implantable device of claim 3, wherein the PRC is selected from the group consisting of benzophenone tetracarboxylic dianhydride, benzoylbenzoic acid, benzoyl benzoyl chloride, 4-benzoylbenzoic acid N-hydroxysuccinimide ester, benzoyl benzoyl amine, substituted phenyl azide and substituted acyl azide.

5. The implantable device of claim 1, wherein the bioactive agent is selected from the group consisting of superoxide dismutase (SOD), super oxide dismutase mimetics (SODm), heparin, polyethylene glycol/oxide, synthetic peptides or natural proteins, nitric oxide donor molecules, and combinations thereof.

6. The implantable device of claim 1, wherein the implantable device is a stent.

7. A method of treating or preventing a disorder, comprising implanting in a human being an implantable device according to claim 1, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

8. A method of treating or preventing a disorder, comprising implanting in a human being an implantable device according to claim 5, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

9. An implantable device comprising a carbon coating and a bioactive agent attached thereto,
wherein the bioactive agent is covalently attached to a photo-reactive chemical (PRC) or a thermo-reactive chemical (TRC), which is in turn covalently attached directly to the carbon coating, and
wherein the carbon coating is a diamond-like carbon coating containing only the elements carbon (C) and hydrogen (H).

10. The implantable device of claim 9, wherein the device is made from bioabsorbable polymers, biostable polymers, a metallic material, or an alloy.

11. The implantable device of claim 9, wherein the bioactive agent is attached to the PRC or the TRC via at least one reactive group.

12. The implantable device of claim 9, wherein the PRC is a compound in the benzophenone family or a compound in the azide family.

13. The implantable device of claim 12, wherein the PRC is selected from the group consisting of benzophenone tetracarboxylic dianhydride, benzoylbenzoic acid, benzoyl benzoyl chloride, 4-benzoylbenzoic acid N-hydroxysuccinimide ester, benzoyl benzoyl amine, substituted phenyl azide, and substituted acyl azide.

14. The implantable device of claim 9, wherein the TRC is selected from the group consisting of acyl peroxide, alkyl peroxide, hydroperoxide, perester, azo compounds, disulfides, and combinations thereof.

15. The implantable device of claim 9, wherein the TRC is selected from the group consisting of acetyl or benzoyl peroxides, cumyl peroxide, t-butyl peroxide, t-butyl hydroperoxide, cumyl hydroperoxide, t-butyl perbenzoate, and azobisisobutylonitrile (AIBN).

16. The implantable device of claim 9, wherein the carbon coating further comprises a metal and/or a ceramic.

17. The implantable device of claim 9, wherein the bioactive agent is selected from the group consisting of superoxide dismutase (SOD), super oxide dismutase mimetics (SODm), heparin, polyethylene glycol/oxide, polyethylene glycol/oxide derivative, sodium hyaluronate and its derivatives, sialic acid, synthetic peptides or natural proteins, synthetic or natural polysaccharides, aloe derived pectin (DelSite Inc.), recombinant human gelatin (Fibrogen), nitric oxide donor molecules, and combinations thereof.

18. The implantable device of claim 9, wherein the bioactive agent is selected from the group consisting of paclitaxel, docetaxel, estradiol, 4-amino-2,2,6,6-tetramethylpiperidine-1-oxyl (4-amino-TEMPO), tacrolimus, dexamethasone, rapamycin, rapamycin derivatives, 40-O-(2-hydroxy) ethyl-rapamycin (everolimus), 40-O-(3-hydroxy)propyl-rapamycin, 40-O-[2-(2-hydroxy) ethoxy]ethyl-rapamycin, 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, pegylated drugs thereof, and combinations thereof.

19. The implantable device of claim 9, wherein the implantable device is a stent.

20. The implantable device of claim 9, wherein the implantable device is a bioabsorbable stent.

* * * * *

UNITED STATES PATENT AND TRADEMARK OFFICE
CERTIFICATE OF CORRECTION

| | | |
|---|---|---|
| PATENT NO. | : 8,128,688 B2 | Page 1 of 1 |
| APPLICATION NO. | : 11/820560 | |
| DATED | : March 6, 2012 | |
| INVENTOR(S) | : Ni Ding et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 259 days.

Signed and Sealed this
Twenty-fourth Day of July, 2012

David J. Kappos
*Director of the United States Patent and Trademark Office*